United States Patent
Li et al.

(10) Patent No.: US 9,909,997 B2
(45) Date of Patent: Mar. 6, 2018

(54) DETECTION SYSTEM BASED ON MODULATION OF LINE STRUCTURED LASER IMAGE OF GLASS

(71) Applicant: LUOYANG LANDGLASS TECHNOLOGY CO., LTD., Henan (CN)

(72) Inventors: Yanbing Li, Henan (CN); Bin Liu, Henan (CN)

(73) Assignee: LUOYANG LANDGLASS TECHNOLOGY CO., LTD, Henan (CN)

( * ) Notice: Subject to any disclaimer, the term of this patent is extended or adjusted under 35 U.S.C. 154(b) by 291 days.

(21) Appl. No.: 14/422,081

(22) PCT Filed: Aug. 23, 2013

(86) PCT No.: PCT/CN2013/082168
§ 371 (c)(1),
(2) Date: Feb. 17, 2015

(87) PCT Pub. No.: WO2014/040486
PCT Pub. Date: Mar. 20, 2014

(65) Prior Publication Data
US 2015/0226682 A1    Aug. 13, 2015

(30) Foreign Application Priority Data

Sep. 14, 2012 (CN) .......................... 2012 1 0340126

(51) Int. Cl.
*H04N 7/18* (2006.01)
*G01N 21/958* (2006.01)
(Continued)

(52) U.S. Cl.
CPC ........... *G01N 21/958* (2013.01); *C03B 35/00* (2013.01); *G01B 11/0691* (2013.01);
(Continued)

(58) Field of Classification Search
CPC ........ H04N 7/13; H04N 3/1525; G01N 21/49;
G01N 21/896; G01N 21/8806; C10B 33/10; G01S 15/8918; C03B 27/0417
See application file for complete search history.

(56) References Cited

U.S. PATENT DOCUMENTS 4,381,675 A * 5/1983 Roberts ............... G01S 15/8918
73/606
RE36,047 E * 1/1999 Gilblom ............... H04N 3/1525
348/295

(Continued)

FOREIGN PATENT DOCUMENTS

CN     1707249 A    12/2005
CN     1759071 A     4/2006
(Continued)

*Primary Examiner* — Sathyanaraya V Perungavoor
*Assistant Examiner* — Patricia I Young
(74) *Attorney, Agent, or Firm* — AKC Patents, LLC; Aliki K. Collins

(57) ABSTRACT

A detection system based on modulation of line structured laser image of glass includes a processing section, a control system, and roller conveying mechanisms. Detection mechanism provided over entrance of the processing section includes shell and camera with laser which emits beam on the surface of the glass in the gap between sliding rollers. Focal plane of the camera corresponds to the beam irradiation surface, and signal output terminal of the camera is connected with the control system in such a way that when glass passes the detection area, laser irradiates the glass surface and the line structured laser is modulated based on the glass to form laser modulation image with distribution of light and shade, staggered movement direction, or distorted laser lines. The camera transmits the captured glass information and parameters to the control system.

10 Claims, 3 Drawing Sheets

(51) Int. Cl.
*G01B 11/25* (2006.01)
*G01N 21/896* (2006.01)
*C03B 35/00* (2006.01)
*G01B 11/06* (2006.01)
*G01B 11/16* (2006.01)
*G01N 21/88* (2006.01)
*H04N 7/00* (2011.01)
*G01N 21/49* (2006.01)

(52) U.S. Cl.
CPC ........ *G01B 11/167* (2013.01); *G01B 11/2518* (2013.01); *G01B 11/2522* (2013.01); *G01N 21/896* (2013.01); *G01N 21/49* (2013.01); *G01N 21/8806* (2013.01); *G01N 2201/06113* (2013.01); *G01N 2201/103* (2013.01); *H04N 7/00* (2013.01)

(56) References Cited

U.S. PATENT DOCUMENTS

| | | | |
|---|---|---|---|
| 8,157,968 B2* | 4/2012 | Sato | C10B 33/10 202/262 |
| 2005/0276467 A1* | 12/2005 | Chen | G01N 21/8806 382/152 |
| 2006/0108346 A1* | 5/2006 | Janhunen | C03B 27/0417 219/388 |
| 2008/0297360 A1* | 12/2008 | Knox | G01N 21/49 340/628 |
| 2010/0087945 A1* | 4/2010 | Nakajima | G02F 1/1303 700/105 |
| 2012/0176490 A1* | 7/2012 | Bonham, Jr. | G01N 21/896 348/86 |

FOREIGN PATENT DOCUMENTS

| CN | 1900701 A | 1/2007 |
|---|---|---|
| CN | 102818538 A | 12/2012 |
| JP | 4362335 B2 | 11/2009 |

\* cited by examiner

DETECTION SYSTEM BASED ON MODULATION OF LINE STRUCTURED LASER IMAGE OF GLASS

TECHNICAL FIELD

The invention is related to a detection system for geometrical parameters of glass, particularly to a detection system based on modulation of line structured laser image of glass.

BACKGROUND ART

Light source combined with camera is developing gradually in the glass industry at present to measure comprehensive geometrical parameters of glass for the purpose of monitoring the production process, such as the disclosed patent of method and equipment for monitoring safe glass production and controlled processing process in which high intensity light source is used to irradiate surface of glass to be detected, and relevant data is analyzed based on the signals of intensity of reflective light received by camera. The method is characterized by three disadvantages: the first is that light received by camera is specular reflection light, which means that what the camera finally obtains is the signal of intensity of light, based on which the data from analysis deviates significantly from the actual parameters of glass; the second is that the equipment is susceptible to external natural light and background colors when it is used, resulting in inaccurate data in measurement; the third is that the equipment or method has special requirements on incident angle of light or angle of the detection surface when it is adopted, and the data obtained from measurement has large errors when the angles deviate.

Invention Contents

The technical issue to be solved by the invention is to provide a detection system based on modulation of line structured laser image of glass which has no special requirements on incident angle of light or angle of the detection surface and obtains highly accurate information and parameters through measurement so as to overcome the shortages existing in the prior art.

The technical scheme adopted by the invention is a detection system based on modulation of line structured laser image of glass, comprising processing section for processing glass, loading table and unloading table provided at both sides of the processing section, control system for controlling operation process of the processing section, roller conveying mechanisms provided on the loading table and the unloading table respectively which are provided with plurality of sliding rollers, the rotation of which will drive glass to be detected to move on the loading table and the unloading table, and detection mechanism provided over entrance of the processing section through support bracket.

The detection mechanism comprises shell, a camera with laser which is enclosed in the shell, and a camera controlling device for initiating the camera at a fixed time whose signal output terminal is connected with the camera and which is used for initiating the camera at a fixed time to scan the area to be detected to generate image; beam emitted by laser, with laser wavelength of 650 nanometers, is used to irradiate the surface of the glass in the gap between sliding rollers; focal plane of the camera corresponds to the beam irradiation surface for the laser and signal output terminal of the camera is connected with the control system in such a way that when glass passes the detection area, line structured laser irradiates the glass surface and is modulated based on variations of inner and outer profiles, edges, ink patterns, thickness and superficial bending of glass to form laser modulation image with distribution of light and shade, staggered movement direction, or distorted laser lines; the camera captures the laser modulation image and transmits the information and parameters on outer profile, inner structural profile, superficial wave form, bending, thickness and ink distribution of the glass to the control system.

Shell of the detection mechanism is provided with heat insulation layer on inner wall and also provided with fan for heat transfer.

The detection mechanism is secured over the entrance of processing section through support bracket.

The camera controlling device provided on roller conveying mechanism is a rotation angle counting transducer which initiates the camera at a fixed time according to the movement speed of glass on top face of sliding roller.

The support bracket is a gantry provided on the loading table through sliding rail which is in a plane parallel to the conveying plane of the roller conveying mechanism, the gantry moves along the direction of the sliding rail, and before glass enters the processing section, the gantry initiates the detection mechanism to scan and collect information on outer profile, inner structural profile, superficial wave form, bending, thickness, ink distribution, etc. of the glass while receiving command from the control system to move along the direction of the sliding rail.

The camera controlling device is a speed transducer which initiates the camera at a fixed time according to the movement speed of the gantry, and the control system controls the glass on the loading table to stop movement during movement of the gantry.

The camera controlling device is a speed transducer which initiates the camera at a fixed time according to the movement speed of the gantry in relation to the movement speed of the glass on roller, and the gantry moves in the same or opposite direction to the glass to be detected on the loading table.

The camera in the detection mechanism is high speed area array CMOS camera.

The laser light emitted by the laser is single-line structured light, or multiple-line structured light, or grid structured light.

A detection mechanism is also provided over the unloading table to detect information on the surface of the tempered glass and transmit the collected information to the control system.

With the above technical schemes, the invention has the following beneficial effects:

First, the detection mechanism in the system, with integral design and compact structure, can be easily fitted over the entrance of the processing section, has strong adaptation capacity to the installation of other processing means, has no special requirements on incident angle of light or angle of the detection surface during detection, and obtains highly accurate data through measurement, moreover, the background light has no impact on accuracy of the measurement.

Second, when the system is adopted to obtain information on load through measurement, beam emitted by the laser irradiate the surface of the glass in the gap between the sliding rollers in roller conveying mechanism, focal plane of the camera is at the height of the surfaces of the sliding rollers in roller conveying mechanism, and signal output terminal of the camera is connected with the control system in such a way that when glass passes the detection area, linear laser irradiates the glass surface and the line structured laser is modulated based on inner and outer profiles, edges, ink patterns printed on glass surface, difference of vertical distances of reference panel with glass product and superficial bending of the glass to form laser modulation image with distribution of light and shade, staggered movement direction, or distorted laser lines; the camera receives the image with morphological change of glass surface, and thus obtains the information and parameters on outer profile, inner structural profile, superficial wave form, bending, thickness, ink distribution, etc. of the glass, by which accuracy is significantly improved as compared with the measuring means in the prior art which rely on light intensity signal to analyze the information on load.

Third, with line structured laser with wavelength of 650 nanometers, beam emitted by the laser and the camera are also placed on the same side of the object to be detected in such a way that impact of background light can be fully neglected for the detection mechanism to achieve the best measurement results and also improve the accuracy in measurement.

Forth, camera controlling device, with its signal output terminal connected to the camera, is also provided for initiating the camera at a fixed time; the camera controlling device initiates the camera at a fixed time according to the operation speed of roller conveying mechanism or initiates the camera to scan the area to be detected to generate image based on the set time to enable the speed for conveying glass or the movement speed of the gantry to match the collection frequency of the camera; the camera will collect information every time when glass and/or camera move(s) for a distance equivalent to that of a detection area in relation to each other to ensure that no area is missed and more accurate detection is achieved.

Fifth, the gantry with detection mechanism is provided on the fixation bracket of roller conveying mechanism through sliding rail, which means that the gantry moves in a plane parallel to the conveying plane of the roller conveying mechanism, in such a way that the gantry moves on the sliding rail, while the detection mechanism located at the gantry initiates detection if glass is on the conveying plane. Such configuration has stronger adaptation to installation of other processing means.

The appended drawing reference signs are shown as follows: 1 refers to product to be detected, 2 refers to processing section, 201 refers to entrance of processing section, 3 refers to loading table, 4 refers to unloading table, 5 refers to roller conveying mechanism, 6 refers to detection mechanism, 601 refers to laser, 602 refers to camera, 7 refers to support bracket, and 8 refers to rotation angle counting transducer.

DETAILED DESCRIPTION

Figure 1:
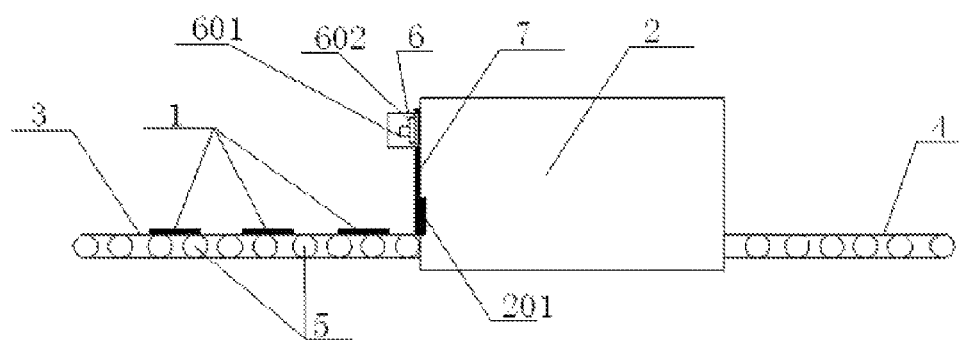
FIG. 1 is the main view of the first embodiment of the invention.
Figure 2:
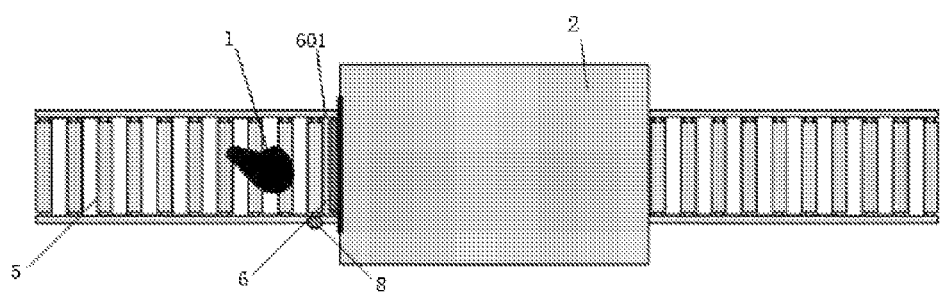
FIG. 2 is the top view of the first embodiment of the invention.

As shown in FIG. 1 and FIG. 2, the detection system based on modulation of line structured laser image of glass comprises processing section 2 for processing glass, loading table 3 and unloading table 4 provided at both sides of the processing section 2, control system for controlling operation process of the processing section, roller conveying mechanisms 5 provided on the loading table 3 and the unloading table 4 respectively which are provided with plurality of sliding rollers, the rotation of which will drive glass to be detected to move on the loading table 3 and the unloading table 4, and detection mechanism 6 provided over entrance of the processing section 201 through support bracket 7.

The detection mechanism 6 comprises shell, a camera 602 with laser 601 which is enclosed in the shell, and a camera controlling device for initiating the camera at a fixed time whose signal output terminal is connected with the camera 602 and which is used for initiating the camera at a fixed time to scan the area to be detected to generate image; the laser 601 in which reddish laser light with wavelength of 650 nanometers is adopted preferably emits beam on the surface of the glass in the gap between sliding rollers, focal plane of the camera 602 corresponds to the beam irradiation surface for the laser, and signal output terminal of the camera 602 is connected with the control system in such a way that there is no information available in image when no glass passes; when glass passes the detection area, linear laser irradiates the glass surface and the line structured laser is modulated based on inner and outer profiles, edges, ink patterns printed on glass surface, difference of vertical distances of reference panel with glass product and superficial bending of the glass to form laser modulation image with distribution of light and shade, staggered movement direction, or distorted laser lines; the camera receives the image with morphological change of glass surface, thus obtains the information and parameters on outer profile, inner structural profile, superficial wave form, bending, thickness, ink distribution, etc. of the glass, and transmits the said parameters to the control system; With the information and parameters obtained above, the control system identifies glass models by adopting the multi-parameter fuzzy matching method and is thus used for intelligent control of parameters for glass production and processing equipment; there shall be included angle between optical axis and imaging axis of camera to ensure that location exposed to the beam is within the imaging scope of the camera, and dark-field imaging is adopted in the device in such a way that the background will basically not be imaged in the camera, therefore, background light will have no impact on accuracy in measurement.

Figure 3:
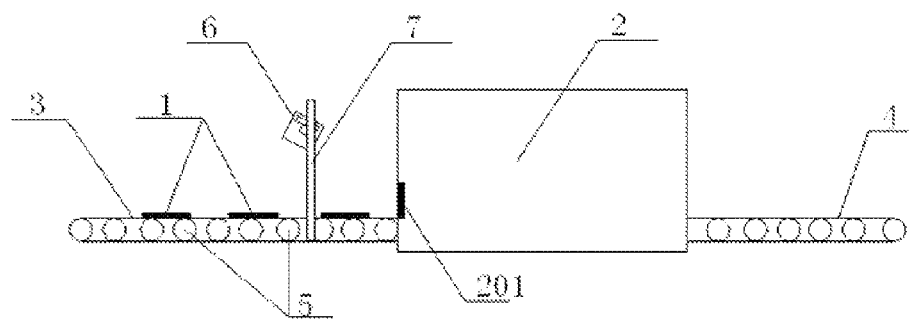
FIG. 3 is the structural schematic diagram of the second embodiment of the invention.
Figure 4:
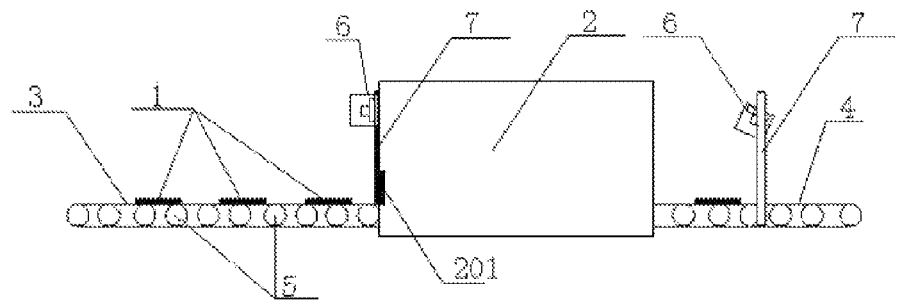
FIG. 4 is the structural schematic diagram of the third embodiment of the invention.

As shown in FIG. 3 and FIG. 4, the detection mechanism 6 is provided over the entrance of the processing section 201 through the support bracket 7 for which two preferred embodiments are available. The first embodiment is that the support bracket is secured at the entrance of the processing section, wherein the camera controlling device can be selected to be the rotation angle counting transducer 8 provided in the roller conveying mechanism which initiates camera at a fixed time according to the calculated linear speed of sliding roller and is provided for the purpose of controlling the speed for conveying glass to match the collection frequency of the camera; the camera will collect information every time when glass travels for a distance equivalent to that of a detection area to ensure that no area is missed and higher accurate detection is achieved. The second embodiment is that the support bracket is movable, wherein its structure can be varied adaptively, and gantry structure can be selected and provided on the loading table 3 through sliding rail that is in a plane parallel to the conveying plane of the roller conveying mechanism 5; the gantry moves along the direction of the sliding rail, which means the gantry moves in a plane parallel to the conveying plane of the roller conveying mechanism 4; the configuration has two detection modes. The first mode is that the glass to be detected is kept still, and the gantry with detection mechanism moves, wherein the camera controlling device can be selected to be speed transducer which initiates the camera 602 at a fixed time according to the movement speed of the gantry to ensure that no area is missed. The second mode is that glass and detection mechanism have two movement modes, i.e. they move in the same direction or opposite direction. In such a way, the gantry with detection mechanism and the glass to be detected have relative movement speed. In this case, the camera controlling device can also be selected to be speed transducer which initiates the camera 302 at a fixed time according to the movement speed of the gantry in relation to the movement speed of the glass on roller and is also provided for the purpose of controlling the camera to collect information every time when glass travels a distance equivalent to that of a detection area to ensure that no area is missed.

Figure 5:
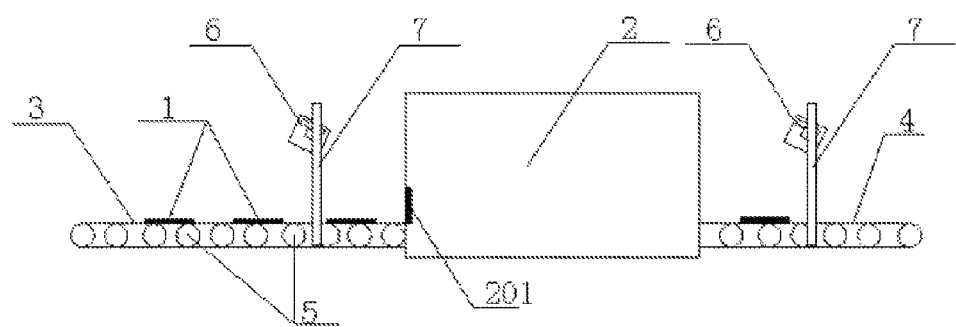
FIG. 5 is the structural schematic diagram of the forth embodiment of the invention.

A detection mechanism 6 adopting the same detection theory with that at the loading table can also be provided on the unloading table 4 at the other side of the processing section 2 to improve the closed-loop control performance of the device. It can also be provided on secured or movable support bracket to detect information on surface of the tempered glass and also transmit the information to the control system. Thus, processing quality and rate of finished products can be analyzed for products through comparison by the control system, and comprehensive production information can also be obtained for the products of the same batch to realize automatic production capacity of the device. As shown in FIG. 4 and FIG. 5, detection mechanism at loading table is secured while that at unloading table is movable in FIG. 4. Detection mechanisms at loading and unloading tables can move to collect information in FIG. 5.

Shell of the detection mechanism is provided with heat insulation layer on inner wall and is also provided with fan for heat transfer.

The camera in the detection mechanism is high speed area array CMOS camera.

The laser light emitted by the laser is single-line structured light, or multiple-line structured light, or grid structured light.

In the invention, the detection mechanism, with integral design and compact structure, can be easily fitted over the entrance of the processing section. The device is enclosed with alloy housing, provided with heat insulation layer on inner wall and provided with fan for heat transfer to ensure operation temperature of laser and CMOS camera in the device.

During operation of the system, the roller conveying mechanism conveys glass product to be detected into the processing section via the entrance of the processing section. While sliding rollers rotate, the detection mechanism is initiated, laser beam is emitted by line structured laser on the face of the glass in the gap between the sliding rollers at certain angle, and the CMOS camera initiates image monitoring for the gap area when focal plane of its lens is at the height of the top surface of sliding roller. When there is no glass passing, imaging plane of the laser beam is not within the imaging area of the CMOS camera, thus image obtained by the CMOS camera contains no information. When glass passes the detection area, the laser beam is modulated based on the glass to form image with information containing disconnection, distribution of light and shade, distortion and differences of locations of feature points with the reference plane in the movement direction due to shape, size, distribution of printed ink patterns, superficial wave form, bending and thickness of the glass. Rotation angle of sliding roller is collected and counted by an angle counting transducer and then triggers the CMOS camera to enable the CMOS camera to fully image the glass (i.e., no area is missed). During feeding of glass product, the collected information on image is processed, profile and comprehensive geometrical parameters are obtained and its model is identified with multi-parameter fuzzy identification method by the device. Arrangement, comprehensive geometrical parameters and profile of the glass are indicated in graphical manner on the industrial computer for testing. Glass model and comprehensive parameters on size are also transmitted to the control system via universal serial interface. The control system then set the parameters for processing automatically based on the obtained comprehensive geometrical parameters of the glass.

The camera in the detection mechanism is high speed area array CMOS camera. Array elements of the camera are relevant to detection accuracy of geometrical parameters based on width of conveying sliding roller of the system. Ratios of length to width of chips are close to each other for conventional area array imaging apparatuses in the prior art. Numbers of array elements in the directions of length and width have little difference. The detection area based on the invention is long and narrow; so, while it ensures the width direction of sliding roller, it results in large coverage area of glass product in the movement direction, therefore, the CMOS camera is selected in the invention to obtain data for the specified number of lines by taking advantage of its bit reading feature. In this way, coverage area of glass in the movement direction is reduced, while data volume is also reduced. This is favorable to the subsequent image processing. It is exemplified by that when coverage area of the system is narrow and long, with the size of 3000 mm*40 mm, and the 4K*3K high speed CMOS camera is selected, then we can enable the chip of the camera to change its operation position to 4K*40 by reading the specified number of lines, and thus the narrow and long detection area can be formed effectively.

Light source in the detection mechanism is line structured laser, either single line structured light or multiple-line structured light. Number of laser beams determines the detection accuracy of size of product in the movement direction at certain collection frame rate.

Total length of conveying sliding roller of the system is fixed, which means that the actual effective length of product to be placed can be determined by the length of conveying sliding roller. Rotation angle counting transducer for sliding roller of the system mainly has two tasks, to determine how long is product conveyed every time when the camera images it, namely, external trigger signal generation function of the CMOS camera, and to determine whether the material enters the section completely, namely, starting and ending signal generation function of the detection device.

When receiving trigger signal from the rotation angle counting transducer, the detection device based on the invention is initiated to collect and expose one frame image of the monitored area and save it in the specified location of the memory; when receiving ending signal from the rotation angle counting transducer, the detection device stops the detection route and starts the processing of image data. It is exemplified by that when single frame image of detection area is of 3000*60 and collection is conducted for 200 times, with data bit depth of 8 bits, then the total data volume is 274 Mbit.

The image processing based on the invention comprises collection and screening of feather points, identification of number of glass sheets, graphic indication of outer profile of glass, thickness of glass, size of glass, wave form of glass, bending, etc., and mathematical characterization of the above parameters. The process can be used not only to establish product database, but also to judge product type through comparison with data in the product database.

The invention claimed is:

1. A detection system based on modulation of line structured laser image of glass, comprising:
a processing section (2) for processing glass, a loading table (3) and an unloading table (4) provided at a side of an entrance and at a side of an exit of the processing section (2), respectively, a control system for controlling operation process of the processing section, roller conveying mechanisms (5) provided on the loading table (3) and the unloading table (4), respectively, which are provided with a plurality of sliding rollers, rotation of which drives glass to be detected to move on the loading table (3) and the unloading table (4), and a detection mechanism (6) provided over the entrance of the processing section (201) through a support bracket (7);
wherein the detection mechanism (6) comprises a shell, a camera (602), a laser (601) which is enclosed in the shell, and a camera controlling device for initiating the camera at a fixed time, whose signal output terminal is connected with the camera (602) and which is used for initiating the camera (602) at a fixed time to scan an area to be detected to generate an image;
wherein a laser beam emitted by the laser (601), has a laser wavelength of 650 nanometers, and is used to irradiate a surface of the glass in a gap area between sliding rollers;
wherein the camera (602) initiates image monitoring of the gap area when a focal plane of the camera (602) is at a height of a top surface of the sliding rollers and a signal output terminal of the camera (602) is connected with the control system in such a way that when glass passes the gap area, the laser beam irradiates the glass and is modulated based on glass properties comprising one of variations of inner and outer profiles, edges, ink patterns, thickness and superficial bending of glass to form a laser modulation image with information comprising one of disconnection, distribution of light and shade, staggered movement direction, or distorted laser lines;
wherein the camera captures the laser modulation image and transmits the information and parameters on outer profile, inner structural profile, superficial wave form, bending, thickness and ink distribution of the glass to the control system.

2. The detection system according to claim 1, wherein the shell of the detection mechanism (6) is provided with a heat insulation layer on an inner wall and also is provided with a fan for heat transfer.

3. The detection system according to claim 1, wherein the detection mechanism (6) is secured to the entrance of the processing section (201) through the support bracket (7).

4. The detection system according to claim 3, wherein the camera controlling device is provided on the roller conveying mechanism (5) and comprises a rotation angle counting transducer (8) which initiates the camera (602) at a fixed time according to a movement speed of the glass on the top surface of the sliding rollers.

5. The detection system according to claim 1, wherein the support bracket (7) is a movable gantry provided on the loading table (3) through a sliding rail which is in a plane parallel to a conveying plane of the roller conveying mechanism (5), and wherein the gantry moves along the direction of the sliding rail, and before the glass enters the processing section, the gantry initiates the detection mechanism (6) to scan and collect information on outer profile, inner structural profile, superficial wave form, bending, thickness, and ink distribution, of the glass while receiving command from the control system to move along the direction of the sliding rail.

6. The detection system according to claim 5, wherein the camera controlling device is a speed transducer which initiates the camera (602) at a fixed time according to a movement speed of the gantry, and the control system controls the glass on the loading table (3) to stop moving during movement of the gantry.

7. The detection system according to claim 5, wherein the camera controlling device is a speed transducer which initiates the camera (602) at a fixed time according to a movement speed of the gantry in relation to a movement speed of the glass on roller, and the gantry moves in the same or opposite direction to the glass to be detected on the loading table (3).

8. The detection system according to claim 1, wherein the camera (602) in the detection mechanism (6) is a high speed area array CMOS camera.

9. The detection system according to claim 8, wherein the laser light emitted by the laser (601) is single-line structured light, or multiple-line structured light, or grid structured light.

10. The detection system according to claim 1, wherein a detection mechanism (6) is also provided over the unloading table (4) to detect information on a surface of the tempered glass and transmit the collected information to the control system.

* * * * *